United States Patent
Wurtman

(10) Patent No.: US 9,572,830 B2
(45) Date of Patent: Feb. 21, 2017

(54) URIDINE EFFECTS ON DOPAMINE RELEASE

(75) Inventor: Richard J. Wurtman, Boston, MA (US)

(73) Assignee: MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 1880 days.

(21) Appl. No.: 11/126,410

(22) Filed: May 11, 2005

(65) Prior Publication Data

US 2006/0025376 A1 Feb. 2, 2006

Related U.S. Application Data

(60) Provisional application No. 60/570,444, filed on May 13, 2004.

(51) Int. Cl.
*A61K 31/7072* (2006.01)
*A61K 31/685* (2006.01)
*A61K 31/513* (2006.01)

(52) U.S. Cl.
CPC .......... *A61K 31/7072* (2013.01); *A23L 33/10* (2016.08); *A23L 33/13* (2016.08); *A61K 31/513* (2013.01); *A61K 31/685* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,789,666 A * | 12/1988 | Gennari | 514/51 |
| 4,960,759 A * | 10/1990 | De Luca et al. | 514/50 |
| 4,994,442 A * | 2/1991 | Gil et al. | 514/45 |
| 5,190,948 A | 3/1993 | Materazzi et al. | |
| 5,470,838 A | 11/1995 | von Borstel et al. | |
| 5,583,117 A | 12/1996 | von Borstel et al. | |
| 5,709,888 A | 1/1998 | Gil et al. | |
| 5,801,160 A * | 9/1998 | Sandage et al. | 514/49 |
| 5,962,459 A * | 10/1999 | Piazza et al. | 514/269 |
| 6,103,703 A | 8/2000 | Renshaw et al. | |
| 6,258,795 B1 * | 7/2001 | von Borstel et al. | 514/49 |
| 6,274,563 B1 | 8/2001 | von Borstel et al. | |
| 6,316,426 B1 | 11/2001 | von Borstel et al. | |
| 6,472,378 B2 | 10/2002 | von Borstel et al. | |
| 6,989,376 B2 * | 1/2006 | Watkins et al. | 514/50 |
| 2003/0114415 A1 | 6/2003 | Wurtman et al. | |
| 2005/0203053 A1 | 9/2005 | Wurtman et al. | |

FOREIGN PATENT DOCUMENTS

| | | |
|---|---|---|
| EP | 0 348 360 A2 | 12/1989 |
| EP | 0484266 A2 | 5/1992 |
| WO | WO 97/45127 A1 | 12/1997 |
| WO | WO 00/06174 A1 | 2/2000 |
| WO | WO 00/11952 A1 | 3/2000 |
| WO | WO 03/041701 A2 | 5/2003 |

OTHER PUBLICATIONS

Barrachina et al., "Neuroprotective effect of citicoline in 6-hydroxydopamine-lesioned rats and in 6-hydroxydopamine-treated SH-SY5Y human neuroblastoma cells", Journal of the Neurological Sciences, 215 (2003) 105-110.*
Barrachina et al. Neuroprotective effect of citicoline in 6-hydroxydopamine-lesioned rats and in 6-hydroxydopamine-treated SH-SY5Y human neuroblastoma cells: (Journal of the Neurological Sciences, 215 (2003) 105-110).
Wurtman et al., "Effect of Oral CDP-Choline on Plasma Choline and Uridine Levels in Humans" Biochem Pharmacol. Oct. 1, 2000;60(7):989-92.
Food and Nutrition Board, Institute of Medicine. Dietary Reference Intakes: Thiamin, Riboflavin, Niacin, Vitamin B-6, Vitamin B-12, Pantothenic Acid, Biotin, and Choline. Washington, DC: National Academy Press, 1998: pp. 390-422.
De Bruin et al., "Combined uridine and choline administration improves cognitive deficits in spontaneously hypertensive rats," Neurobiology of Learning and Memory, vol. 80, 2003, pp. 63-79, XP002603409.
Database WPI, Week 200170, Thomson Scientific, London, GB, AN-2001-610004 & JP 2001233776 A (Yamasa Shoyu KK), Aug. 28, 2001.
Koizumi et al., "Inhibition by Zn2+ of uridine 5'-triphosphare-induced Ca(2+)-influx but not Ca(2+)-mobilization in rat phaeochromocytoma cells" British Journal of Pharmacology, vol. 115, No. 8, Aug. 1995, pp. 1502-1508.
Supplementary European Search Report for corresponding EP application No. 05750060, dated Feb. 18, 2010.

* cited by examiner

*Primary Examiner* — Traviss C McIntosh, III
(74) *Attorney, Agent, or Firm* — Mark S. Cohen; Pearl Cohen Zedek Latzer Baratz LLP

(57) ABSTRACT

The present invention provides methods for increasing secretion of dopamine and other neurotransmitters and treating or reducing the incidence of diseases involving decreased secretion of dopamine and other neurotransmitters, e.g. Parkinson's disease, comprising administering to the subject a uridine or a source thereof, and compositions for treating or reducing an incidence of Parkinson's disease, comprising a uridine, a uridine monophosphate, or a source thereof.

12 Claims, 2 Drawing Sheets

URIDINE EFFECTS ON DOPAMINE RELEASE

CROSS REFERENCE TO RELATED APPLICATION

This application claims priority of U.S. Provisional Application Ser. No. 60/570,444, filed May 13, 2004, which is hereby incorporated in its entirety by reference herein.

The present invention was made in whole or in part with government support under grant number MH 28783 awarded by the National Institutes of Health. The government may have certain rights in the invention.

FIELD OF THE INVENTION

The present invention provides methods for increasing secretion of dopamine and other neurotransmitters and treating or reducing the incidence of diseases involving decreased secretion of dopamine and other neurotransmitters, e.g. Parkinson's disease, comprising administering to the subject a uridine or a source thereof, and compositions for treating or reducing an incidence of Parkinson's disease, comprising a uridine, a uridine monophosphate, or a source thereof.

BACKGROUND OF THE INVENTION

Parkinson's disease (PD) is a common disabling disease of old age affecting about one percent of the population over the age of 60 in the United States. The disease is associated with a reduction in dopamine release from the corpus striatum, leading to severe imbalance of dopamine/acetylcholine in the brain. Dopamine acts in the brain as a neurotransmitter in the synaptic cleft of the neurons, promoting signal transmission between cells.

Parkinson's is a progressively degenerative disease characterized by, among other symptoms, muscle rigidity, coarse tremors and postural deformity. Most conventional treatment methods try to ameliorate the resulting chemical imbalance by either reducing acetylcholine production and/or increasing dopamine concentration, with accompanying side effects that are the result of the new balance attained. One such method of treating PD involves the administration of a dopamine precursor like L-DOPA to promote dopamine release and the stimulation of its post-synaptic receptors. However, L-DOPA has a short half-life in the body and the effect of L-DOPA eventually becomes sporadic and unpredictable, resulting in fluctuations in motor function, dyskinesias and psychiatric side effects.

Thus, there is a need for a treatment of conditions characterized by decreased dopamine release. It is also desirable to have a treatment that will delay the onset of symptoms, and/or alleviate or retard symptomatic expression of the disease.

SUMMARY OF THE INVENTION

The present invention provides methods for increasing secretion of dopamine and other neurotransmitters and treating or reducing the incidence of diseases involving decreased secretion of dopamine and other neurotransmitters, e.g. Parkinson's disease, comprising administering to the subject a uridine or a source thereof, and compositions for treating or reducing an incidence of Parkinson's disease, comprising a uridine, a uridine monophosphate, or a source thereof.

In one embodiment, the present invention provides a method for stimulating or enhancing dopamine release from a neuron, the method comprising contacting the neuron with a uridine or a uridine source, wherein the contact stimulates or enhances dopamine release from the neuron, thereby stimulating or enhancing dopamine release from a neuron.

In another embodiment, the present invention provides a method for treating a Parkinson's disease in a subject, comprising administering to the subject a uridine or a source thereof, wherein administration of the uridine or source thereof stimulates or enhances neuron dopamine levels in the brain of the subject, thereby treating Parkinson's disease in a subject.

In another embodiment, the present invention provides a method of reducing an incidence of a Parkinson's disease in a subject, comprising administering to the subject a uridine or a source thereof, wherein administration of the uridine or source thereof stimulates or enhances neuron dopamine levels in the brain of the subject, thereby reducing an incidence of a Parkinson's disease in a subject.

In another embodiment, the present invention provides a composition for treating or reducing an incidence of Parkinson's disease, comprising a uridine or a source thereof at a dose sufficient to stimulate or enhance dopamine release from a neuron.

DETAILED DESCRIPTION OF THE INVENTION

Figure 1:
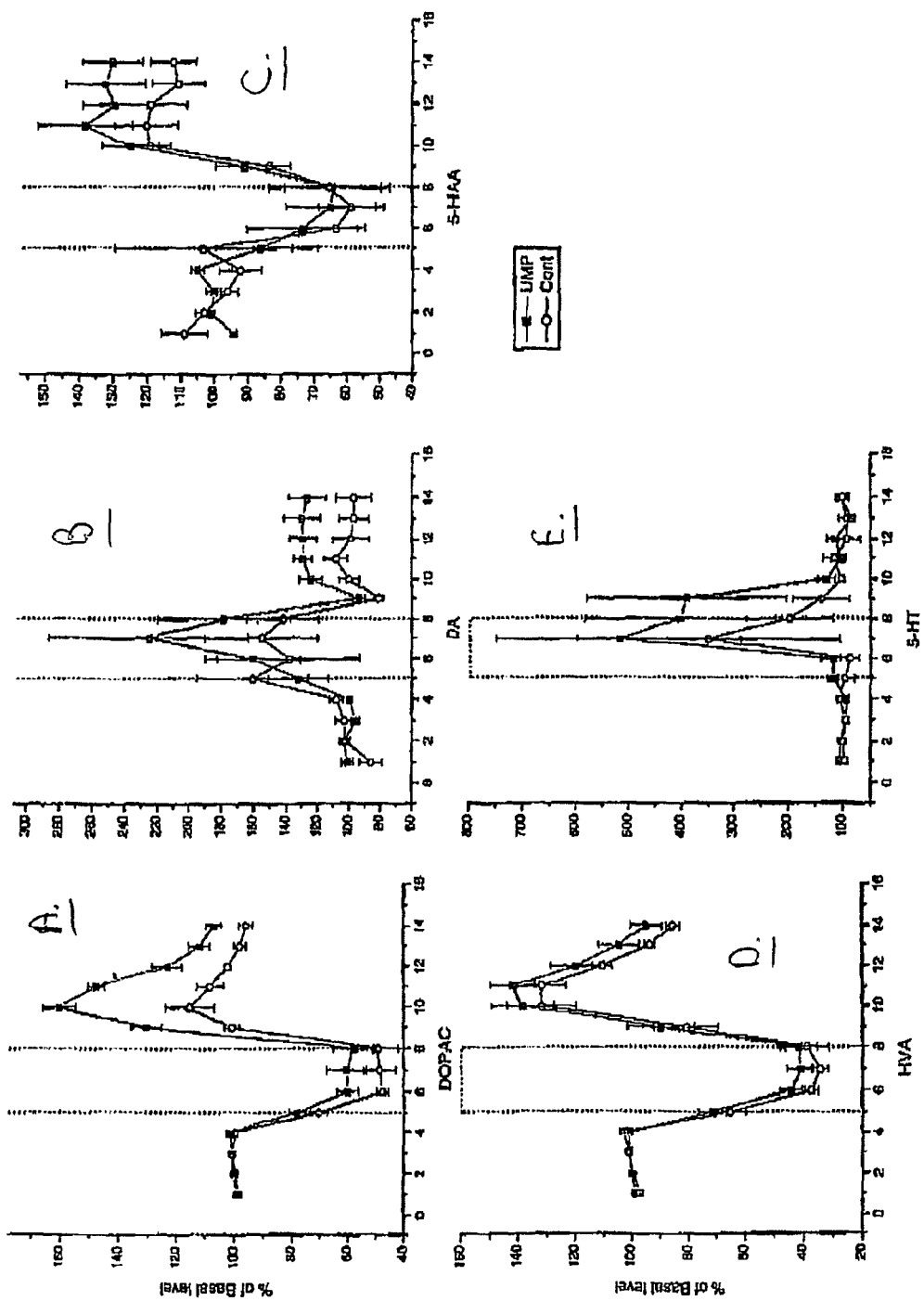
FIG. 1 depicts effects of UMP administration on release of dopamine, 5-HT, and dopamine metabolites before, during and after depolarization in response to stimulation by potassium in the brains of a uridine-fed rat (solid squares) and a control rat (open squares). Depicted are DOPAC (A), dopamine (b), 5-HAA (C), and HVA (D), and 5-HT (E). Error bars reflect differences between repeated stimulations.

The present invention provides methods for increasing secretion of dopamine and other neurotransmitters and treating or reducing the incidence of diseases involving decreased secretion of dopamine and other neurotransmitters, e.g. Parkinson's disease, comprising administering to the subject a uridine or a source thereof, and compositions for treating or reducing an incidence of Parkinson's disease, comprising a uridine, a uridine monophosphate, or a source thereof.

In one embodiment, the present invention provides a method for stimulating or enhancing dopamine release from a neuron, the method comprising contacting the neuron with a uridine or a uridine source, wherein the contact stimulates or enhances dopamine release from the neuron, thereby stimulating or enhancing dopamine release from a neuron.

In another embodiment, the present invention provides a method for treating a Parkinson's disease in a subject, comprising administering to the subject a uridine or a source thereof, wherein administration of the uridine or source thereof stimulates or enhances neuron dopamine levels in the brain of the subject, thereby treating Parkinson's disease in a subject.

In another embodiment, the present invention provides a method of reducing an incidence of a Parkinson's disease in a subject, comprising administering to the subject a uridine or a source thereof; wherein administration of the uridine or source thereof stimulates or enhances neuron dopamine levels in the brain of the subject, thereby reducing an incidence of a Parkinson's disease in a subject.

The uridine or a uridine source is administered, in one embodiment, at a dose sufficient to stimulate or enhance neuron levels of dopamine, 5-HT, or a dopamine metabolite.

In another embodiment, methods of a present invention are utilized to stimulate or enhances release of 5-HT from the neuron. In another embodiment, methods of a present invention are utilized to stimulate or enhances release of serotonin. In another embodiment, methods of a present invention are utilized to stimulate or enhances release of acetyl choline. In another embodiment, methods of a present invention are utilized to stimulate or enhances release of GABA. In another embodiment, methods of a present invention are utilized to stimulate or enhances release of glutamate. In another embodiment, methods of a present invention are utilized to stimulate or enhances release of adenosine. Each possibility represents a separate embodiment of the present invention.

In another embodiment, stimulation or enhancement of release of one of the above neurotransmitters or metabolites refers to the relative increase in the compound released by the neuron, relative to the basal level. In another embodiment, stimulation or increase in dopamine release refers to an increase in absolute concentration or amount. In another embodiment, stimulation or increase in dopamine release refers to an increase in percentage of dopamine released into the nigrostriatal ECF. Neurons of the substantia nigra (brainstem) project to the striatal region of the brain.

As shown in the present invention, dopamine release was significantly enhanced in rats fed a diet enriched in uridine monophosphate. Dietary consumption of UMP also enhanced serotonin release.

In one embodiment, "Stimulated" or "enhanced" release in methods of the present invention refers to the stimulated or enhanced release of the neuromodulators 5-hydroxytryptamine (serotonin) acetylcholine and gamma-aminobutyric acid (γ-aminobutyric acid, GABA) from neurons to synaptic terminals. In another embodiment, excitatory exogenous amino acids, such as glutamate and aspartate are released, as the result of changes in $Ca^{2+}$ concentration across neuronal membranes. In another embodiment, uridine derived from the diet enters the bloodstream and crosses the blood brain barrier as an exogenous amino acid directly accessing the synaptic terminals, where it is converted to UTP and then, in part, to CTP.

In one embodiment, release of dopamine, 5-HT, or a dopamine metabolite is measured in vivo via microdialysis of samples retrieved from a cannula implanted within the right corpus striatum, as exemplified herein. In another embodiment, the method is utilized for measurements of dopamine dihydroxyphenylacetic acid (DOPAC), homovanillic acid (HVA), serotonin or 5-hydrozyindoleacetic acid (5-HIAA) release. In another embodiment, samples are assayed via High Pressure Liquid Chromatography (HPLC), or through any other means known to one skilled in the art. In another embodiment, neurotransmitter levels are assayed by measuring the faradaic current at the respective oxidation potentials with a carbon fiber electrode. In another embodiment, neurotransmitter levels are assayed by any other method known in the art for measuring neurotransmitter levels. Each possibility represents a separate embodiment of the present invention.

In another embodiment, the present invention provides a composition for treating or reducing an incidence of Parkinson's disease, comprising a uridine or a source thereof at a dose sufficient to stimulate or enhance dopamine release from a neuron of a subject.

In another embodiment, the methods and compositions of the present invention are utilized to treat or reduce the incidence of a symptom associated with Parkinson's disease. In one embodiment, alleviation of the symptoms associated with Parkinson's disease is assessed by production of a change in the score from baseline of the pertinent United Parkinson's disease Rating Scale (UPDRS) levels, wherein the changes are indicative between release and cumulative within levels, and comprise changes in: Part I—mentation/behavior/mood, Part II—activities of daily living, Part III—motor examination, Part IV—levodopa complications.

In one embodiment, the symptom associated with Parkinson's disease is muscle rigidity. In another embodiment, the symptom is coarse tremors. In another embodiment, the symptom is postural deformity. In another embodiment, the symptom is rigidity. In another embodiment, the symptom is slow movement. In another embodiment, the symptom is poor balance. In another embodiment, the symptom is any other symptom associated with Parkinson's disease known in the art. Each possibility represents a separate embodiment of the present invention.

In one embodiment, the term "contacting a neuron" in methods of the present invention refers to direct exposure of the neuron to the uridine or uridine source. In another embodiment, the term "contacting a neuron" refers to indirect exposure of the neuron to the uridine or uridine source. In another embodiment, contact with a uridine or uridine source results in an indirect supply to the neuron, such as via the diet or via intravenous injection. In another embodiment, contacting a neuron comprises direct contact of the neuron with a uridine or uridine source, which may be accomplished through any means well known in the art, such as injection. Each possibility represents a separate embodiment of the present invention.

In one embodiment of methods and compositions of the present invention, the uridine or source thereof, e.g. UMP, is administered to the subject at a dose of between about 550 to about 700 milligrams. In another embodiment, the uridine or source thereof is administered to the subject at a dose of about 625 milligrams. In one embodiment of methods and compositions the present invention, the uridine or uridine source is administered at a dose of between about 100 and about 4000 milligrams per day (mg/day). In another embodiment, the uridine or uridine source is administered between about 200 and about 800 mg/day.

In another embodiment, the dose of the uridine or uridine source provided is expressed in terms of uridine equivalents. "Uridine equivalent" refers, in one embodiment, to an amount of a compound that, when metabolized, will yield a particular amount of uridine, e.g. 1 mole. Thus, in one embodiment, the uridine or source thereof is administered to the subject at a dose equivalent to about 350 to about 500 milligrams of uridine. In another embodiment, the uridine or source thereof is administered to the subject at a dose equivalent to about 415 milligrams of uridine In another embodiment of methods of the present invention, the uridine or uridine source is administered to a subject at a dosage of between about 40 to about 4000 mg. In another embodiment, the dosage is 40 to about 140 mg/Kg, or in another embodiment, 140 to about 240 mg/Kg, or in another embodiment, 240 to about 340 mg/Kg, or in another embodiment, 340 to about 440 mg/Kg, or in another embodiment, 440 to about 540 mg/Kg, or in another embodiment, 540 to about 640 mg/Kg, or in another embodiment, 640 to about 750 mg/Kg, or in another embodiment, 750 to about 1000 mg/Kg, or in another embodiment, 1000 to about 1250 mg/Kg, or in another embodiment, 1250 to about 1500 mg/Kg, or in another embodiment, 1500 to about 1750 mg/Kg, or in another embodiment, 1750 to about 2000 mg/Kg, or in another embodiment, 2000 to about 2500 mg/Kg, or in another embodiment, 2500 to about 3000 mg/Kg, or in another embodiment, 3000 to about 4000 mg/Kg.

In another embodiment, the uridine or uridine source is provided at a daily dose of 1 to 300 grams, or in another embodiment, 1 to 25 grams, or in another embodiment, 25 to 50 grams, or in another embodiment, 25 to 100 grams, or in another embodiment, 25 to 75 grams, or in another embodiment, 50 to 100 grams, or in another embodiment, 100 to 150 grams, or in another embodiment, or in another embodiment, 50 to 150 grams, or in another embodiment, 25 to 150 grams, or in another embodiment, 75 to 150 grams, or in another embodiment, 150 to 200 grams, or in another embodiment, 125 to 200 grams, or in another embodiment, 125 to 250 grams, or in another embodiment, 200 to 250 grams, or in another embodiment, 250 to 300 grams. Each of the above dosages represents a separate embodiment of the present invention.

In another embodiment, the present invention provides a method of treating or preventing a disease or condition in a subject, wherein the disease or condition is alleviated by increased dopamine levels, the method comprising administering to the subject a composition comprising a uridine or a source thereof, wherein administration of the uridine or source thereof stimulates or enhances neuron dopamine levels, thereby treating or preventing a neurological disease in a subject. In one embodiment, stimulating or enhancing neuron dopamine release alleviates a symptom of the disease or condition.

In one embodiment, the disease or condition is a neurodegenerative disease. In another embodiment, the disease or condition is neurological. In another embodiment, the disease or condition is Alzheimer's disease (AD). In another embodiment, the disease or condition is dementia with Lewy Bodies (DLB). In another embodiment, the disease or condition is multi-infarct dementia. In another embodiment, the disease or condition is Attention Deficit Hyperactivity Disorder (ADHD). In another embodiment, the disease or condition is Restless Legs (RL). In another embodiment, the disease or condition is age-related tremors. In another embodiment, the disease or condition is or schizophrenia. In another embodiment, the disease or condition is inappropriate sleepiness in narcolepsy. In another embodiment, the disease is schizophrenia. In another embodiment, the disease or condition is attention deficit hyperactivity disorder (ADHD).

In another embodiment, the disease or condition is narcoplesy. In another embodiment, the disease or condition is cognitive disturbances associated with age or vascular disease. In another embodiment, the disease is hyperprolactmenia. In one embodiment, the disease is chronic. In another embodiment, the disease is acute. Each possibility represents a separate embodiment of the present invention.

In another embodiment, the compositions and their use in the methods of the present invention are utilized for lowering excessively high levels of the hormone prolactin, such as, for example, in subjects with pituitary tumors or those who have taken drugs to raise prolactin levels. Dopamine acts on the pituitary as an inhibitor of prolactin secretion. In another embodiment, the methods and compositions of the present invention are utilized for improving cognitive abilities or the initiation of behavior in people with disturbances related to age or vascular disease. Each possibility represents a separate embodiment of the present invention.

In another embodiment, the disease or condition results in inappropriate sleepiness, high levels of the hormone prolactin, or poor cognitive ability. In another embodiment, the inappropriate sleepiness, high levels of the hormone prolactin, or poor cognitive ability results from age or vascular disease. Each possibility represents a separate embodiment of the present invention.

In another embodiment, the methods of the present invention are used for alleviating symptoms of a neurological disease. In one embodiment, the symptom is tremors. In another embodiment, the symptom is unsteady gait. In another embodiment, the symptom is vision effects. In another embodiment, the symptom is difficulty swallowing. In another embodiment, the symptom is dry mouth. In another embodiment, the symptom is urine retention. In another embodiment, the symptom is stooped posture. In another embodiment, the symptom is disturbances of consciousness. In another embodiment, the symptom is restlessness. In another embodiment, the symptom is lack of concentration. In another embodiment, the symptom is hyperactivity. In another embodiment, the symptom is depression. In another embodiment, the symptom is insomnia. In another embodiment, the symptom is hallucinations. In another embodiment, the symptom is tics. In another embodiment, the symptom is uncontrollable utterances. In another embodiment, the symptom is convulsions. In another embodiment, the symptom is incontinence. In another embodiment, the symptom is impotence. In another embodiment, the symptom is erectile dysfunction. In another embodiment, the symptom is lack of coordination. Each possibility represents a separate embodiment of the present invention.

In one embodiment, the neurological disease treated by a method of the present invention is a chronic disease, and administration of a composition comprising a uridine or uridine source stimulates or enhances dopamine release. In one embodiment, the composition comprising a uridine or uridine source is administered throughout the course of disease. In another embodiment, the uridine or uridine source or compositions of the present invention are administered during symptomatic stages of the disease. In another embodiment, the uridine or uridine source is administered as a pretreatment for prevention of the disease. In another embodiment, the uridine or uridine source or compositions of the present invention are administered as a post-treatment for preventing relapse of the disease. Each possibility represents a separate embodiment of the present invention.

In another embodiment, the uridine or uridine source of the present invention is administered in cycles. In one embodiment, administration in cycles refers to the steps of providing the uridine or uridine source, or compositions of the present invention for a specified period of time, ceasing the administration, and re-administering the uridine or uridine source, or compositions of the present invention, for a second period of time. In another embodiment, the steps are repeated and are dependent upon the severity of symptoms. According to this aspect of the invention, and in one embodiment symptoms at a severity of the United Parkinson's disease Rating Scale (UPDRS) of III necessitate treatment according to the methods of the present invention.

In another embodiment, the methods of treating or preventing a neurological disease in the present invention are for diseases which are acute. In one embodiment, a single administration of the composition comprising a uridine or uridine source is administered, or in another embodiment, the administration is for the duration of the acute phase of the disease. In another embodiment, the administration is for the duration of the disease, and a prescribed period following the disease, whether the disease is acute or chronic. Each possibility represents a separate embodiment of the present invention.

In one embodiment, the administration of the uridine or uridine source serves to prevent or treat relapse of a neurological disease. In another embodiment, the administration of the uridine or uridine source serves to delay the onset of the neurological disease, or in another embodiment, reduce its severity. Each possibility represents a separate embodiment of the present invention.

In another embodiment, the present invention provides a composition for treating or preventing a neurological disease, comprising a uridine or uridine source at a concentration sufficient to stimulate or enhance neuron dopamine release. It is to be understood that any composition of the present invention may be utilized for the methods of the present invention.

In another embodiment of methods of the present invention, the composition is administered for a period of time of between about 2 and 12 weeks. In another embodiment, the composition is administered for between about 5 and 7 weeks. In another embodiment, the composition is administered for between about 4 and 9 weeks. In another embodiment, the composition is administered for a period of time of between 2 and 12 weeks, or in another embodiment, 2 and 3 weeks, or in another embodiment, 3 and 4 weeks, or in another embodiment, 4 and 5 weeks, or in another embodiment, 5 and 6 weeks, or in another embodiment, 6 and 7 weeks, or in another embodiment, 7 and 8 weeks, or in another embodiment, 8 and 9 weeks, or in another embodiment, 9 and 10 weeks, or in another embodiment, 10 and 12 weeks, or in another embodiment, 5 and 7 weeks, or in another embodiment, a combination thereof.

In another embodiment, the composition comprises a nutritional supplement. In one embodiment, the supplement comprises a choline source. In another embodiment, the supplement comprises a vitamin. In another embodiment, the supplement comprises any other nutritional substance known in the art. Each possibility represents a separate embodiment of the present invention.

The terms "uridine source," "choline source," etc, refer, in one embodiment, to dietary precursors digested in body or converted via enzymatic reaction to form choline. In various other embodiments, "choline source" refers to synthetically produced choline, choline directly obtained via dietary sources, or enzymatically produced, or combinations thereof, including acceptable salts and chelates. Each possibility represents a separate embodiment of the present invention.

In one embodiment, the uridine source of methods and compositions of the present invention is uridine monophosphate (UMP). In another embodiment, the uridine source is uridine diphosphate (UDP). In another embodiment, the uridine source is uridine triphosphate (UTP). In another embodiment, the uridine source is uracil. In another embodiment, the uridine source is UDP-glucose. In another embodiment, the uridine source is UDP-galactose. In another embodiment, the uridine source is UDP-glucuronic acid. In another embodiment, the uridine source is 5-bromo-2-deoxy-uridine (BrdU). In another embodiment, the uridine source is dihydrouridine. In another embodiment, the uridine source is orotidine 5'-phosphate. In another embodiment, the uridine or uridine source may be purified from any number of sources, converted or synthesized. In another embodiment, the uridine source is any other uridine source known in the art. Each possibility represents a separate embodiment of the present invention.

In various embodiments, the choline source of methods and compositions of the present invention is a lecithin, phosphatidylcholine, acetylcholine, alpha-glycerophosphorylcholine or citicholine. In one embodiment, the citicholine is a cytidine 5'-diphosphocholine. Each possibility represents a separate embodiment of the present invention.

In another embodiment, the composition comprises a vitamin or microelement. In various embodiments, the vitamin is a Thiamin (B1), Riboflavin (B2), Niacin (B3), Pantothenic acid (B5), Pyridoxine (B6), Cobalamine (B12), Folic acid, Retinol (A), Tocopherol (E), Ascorbic Acid (C), Calciferol (D), or phylloquinone (K1). In another embodiment, the microelement is Zink, Iron, Copper, Manganese, Calcium, Cobalt, Phosphorous, Iodine, Magnesium, Selenium, Chromium, Molybdenum, Boron, Nickel or Vanadium. In another embodiment, the composition comprises any pharmaceutically acceptable chelate of one of the above vitamins. Each possibility represents a separate embodiment of the present invention.

In other embodiments, the composition may further comprise antioxidants, fiber, herbs (e.g., ginkgo biloba, ginseng) or other nutritional supplements. Selection of one or several of these ingredients is a matter of formulation design, consumer and end-user preference. The amount of these ingredients added to the nutritional supplements of the present invention are readily known to the skilled artisan and guidance to such amounts can be provided by the RDA and DRI (Dietary Reference Intake) doses for children and adults.

It is to be understood that the compositions for use in the methods of the present invention may comprise any combination of any of the components listed herein, and each is to be considered a separate embodiment of the present invention.

In another embodiment, the composition comprises a source of protein. In one embodiment, protein may include whey protein, whey protein concentrate, whey powder, egg, soy protein, soy protein isolate, caseinate (e.g., sodium caseinate, sodium calcium caseinate, calcium caseinate, or potassium caseinate), animal and vegetable protein, or mixtures thereof.

In another embodiment, the nutritional preparation may take any form that is suitable for human or animal consumption. In another embodiment, the composition is a powdery mixture, which is suspendable, dispersible or emulsifiable in a liquid for human or animal consumption. The liquid is, in one embodiment, a water-containing liquid e.g. water, coffee, tea or juice. For such a purpose, the composition is, in one embodiment, be packed in a package intended for covering part of or the total nutritional requirement for a defined period of time. In another embodiment, the present invention provides the nutritional preparation in the form of a dietary supplement.

In another embodiment, the nutritional preparation is a functional food or drink, i.e. a readily obtainable edible or drinkable substance that is supplemented with a composition of the present invention to provide a medical or pharmaceutical effect. Accordingly, the present invention provides a composition of the present invention for use as a functional food ingredient. Functional foods and drinks are, in one embodiment, selected from the group consisting of diary products, such as yogurt and yogurt ice cream, juice, such as orange juice or tomato juice, ready made liquids for drinking, a spreadable product such as e.g. a margarine or a vegetable or plant extracted oil, a cereal product, such as a traditional breakfast cereal product, nutritional bars, biscuits, bread, soups, such as tomato soup, a meat product, such as a hamburger, a meat substitute product, and a vegetable product. In another embodiment, a nutritional preparation of the present invention may be in the form of a ready made liquid or in a powder form or in the form of a troche, a solid composition such as a nutritional bar, a fruit bar, a cookie, a cake, a bread or a muffin. Each possibility represents a separate embodiment of the present invention.

In another embodiment, the composition is formulated for immediate release. In another embodiment, the composition is formulated for controlled or sustained release. Each possibility represents a separate embodiment of the present invention.

The term "controlled release" refers, in various embodiments, to a formulation wherein uptake or release is delayed, pulsed or sustained. In another embodiment, controlled release formulations include implants or microencapsulated delivery systems. In another embodiment, biodegradable, or biocompatible polymers, such as ethylene vinyl acetate, polyanhydrides, polyglycolic acid, collagen, polyorthoesters, or polylactic acid are used in such formulations. Methods for preparation of such formulations are well to those skilled in the art. Each possibility represents a separate embodiment of the present invention.

In another embodiment, the term "sustained release" refers to a dosage form designed to release the composition therefrom for a time period ranging from at least about 0.0005 to about 21, or, in another embodiment, at least about 1 to about 120, days. Release over a longer time period is also contemplated as "sustained release" in the context of the dosage form of the present invention. It is contemplated that sustained release dosage forms for systemic administration as well as local administration can be employed in the practice of the invention. Each possibility represents a separate embodiment of the present invention.

In another embodiment, the composition further comprises a fiber source, a stabilizer, an emulsifier, a flavor source, or a combination thereof. In another embodiment, the fiber source is a high methoxy pectin, low methoxypectin, melanin, lignin, cellulose, hemicellulose, leutein, or a combination thereof.

In other embodiments, the stabilizer comprises lactose, microcystalline cellulose, hydroxymethyl cellulose, starch, waxy maize, xanthan, carageenan, pectin, guar, gum arabic, Konjac, gum tragacanth, propylene glycol alginate, or a combination thereof.

In other embodiments, the emulsifier is lecithin, sodium stearoyl lactylate (ssl), sorbitan fatty acid esters, polyoxyethylene sorbitan fatty acid esters, mono-and di-glycerides, polyoxyethylene fatty acid esters, polyoxyethylene alcohols, egg yolk, enzyme-modified egg yolk, or a combination thereof.

In another embodiment, flavors, coloring agents, spices, nuts or mixtures thereof are incorporated into the product. Flavorings can be e.g. flavored extracts, volatile oils, chocolate flavorings (e.g., non-caffeinated cocoa or chocolate, or chocolate substitutes, such as carob), peanut butter flavoring, cookie crumbs, crisp rice, vanilla or any commercially available flavoring. Flavorings can be protected with mixed tocopherols. Examples of useful flavorings include but are not limited to pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, cherry oil, walnut oil, cinnamon oil, clove oil, or peppermint oil; peanut butter, chocolate flavoring, vanilla cookie crumb, butterscotch and toffee. In another embodiment, the composition contains berry or other fruit flavors. In another embodiment, the composition is further coated, for example with a yogurt coating, if it is produced as a bar.

In another embodiment, the composition comprises an artificial sweetener. In various embodiments, the artificial sweetener is a saccharide, cyclamate, aspartamine, aspartame, acesulfame K, sorbitol, or a combination thereof.

In another embodiment, the composition comprises a preservative. In various embodiments, the preservative is potassium sorbate, sodium sorbate, potassium benzoate, sodium benzoate or calcium disodium EDTA.

In another embodiment of the methods of the present invention, the composition is administered orally. In other embodiments, the composition is administered rectally, topically, buccally (e.g. sub-lingual), intranasally, via aerosolization or parenterally (e.g. subcutaneously, intramuscularly, intradermally, transdermally or intravenously). Each possibility represents a separate embodiment of the present invention.

In another embodiment of the present invention, the composition comprising uridine is in the form of a pill, capsule, gel-cap, suspension, emulsion, patch, ointment, injectable solution or any other delivery means as will be known to one skilled in the art. In one embodiment, the composition may be in the form of a gum, candy, beverage, frozen confection, or food product, such as a bar. The composition can be formulated for single or multiple daily administration.

Each of the above additives, excipients, etc. represents a separate embodiment of the present invention.

In another embodiment, a method of the present invention further comprises administration of an additional Parkinson's medication. In one embodiment, the additional medication is levodopa In another embodiment, the additional medication is carbidopa. In another embodiment, the additional medication is pramipexole dihydrochloride. In another embodiment, the additional medication is ropinirole hydrochloride. In another embodiment, the additional medication is tolcapone bromocriptine. In another embodiment, the additional medication is pergolide. In another embodiment, the additional medication is selegiline hydrochloride. In another embodiment, the additional medication is apomorphine. In another embodiment, the additional medication is any other Parkinson's medication known in the art. Each possibility represents a separate embodiment of the present invention.

In another embodiment, a method of the present invention further comprises administration of a Parkinson's therapy. In one embodiment, the Parkinson's therapy is Activa Tremor Control Therapy. In other embodiments, the Parkinson's therapy is implantation of porcine fetal neural dopaminergic cells or Sertoli cells. In other embodiments, the Parkinson's therapy is implantation of allogeneic human retinal pigment epithelial cells. In other embodiments, the Parkinson's therapy is any other Parkinson's therapy known in the art. Each possibility represents a separate embodiment of the present invention.

Experimental Details

Effects of Oral UMP on Neurotransmitter Release during and following Neuron Depolarization Material and Methods Rats Retired breeder rats consumed a diet containing normal chow (Harlan Tech Lad, Madison, Wis.) supplemented with or without uridine 5'-monophosphate (UMP) (2.5%, w/w)— at a final concentration of 500 mg/kg/day, for a period of six weeks.

Microdialysis

Microdialysis was performed with cannulas implanted directly within the right corpus striatum of the control and treated rats. Cannulas were implanted on day 1, and samples were collected on days 3 and 4. Micro-dialysates (22.5 microliter, collected over 15 minutes) were assayed for dopamine (DA), 3,4-dihydroxyphenylacetic acid (DOPAC), homovanillic acid (HVA), 5-hydroxy-tryptamine (5-HT) and 5-hydroxyindoleacetic acid (5-HIAA). Real-time neurotransmitter level measurements were taken on samples drawn prior to and following depolarization of the neuron membrane via local application of 100 nm potassium chloride (KCl) solution. Animals were then sacrificed, and striatum, hippocampus and temporal cortex were assayed for DA, DOPAC, HVA, 5HT, 5HIAA, DNA, protein and phosphatidyl choline (PC) content.

Analysis of Dopamine and Metabolites

DA and metabolites in dialysates and tissue samples were determined using an ESA Coulochem 11 5100A detector (E1=−175 mV; E2=+325 mV; Eguard=350 mV) with an ESA Microdialysis Cell (model 5014B, ESA, North Chelmsford, Mass.). The mobile phase (MD-TM, ESA) consisted of 75 mM $NaH_2PO_4$, 1.7 mM 1-octanesulfonic acid, 100 ?l/L Triethylamine, 25 ?M EDTA, 10% acetonitrile, pH 3.0. The flow rate was 0.4 mL/min. The column (ESA MD 150, 3×150 mm, 3 ?m, 120 Å) was kept in a 40° C. column oven. Samples were injected to HPLC by an Alltech 580 autosampler (Alltech, Deerfield, Ill.) and maintained to 4° C. with a cooling tray during analysis. Data were captured by Alltech AllChrom™ data system, and analyzed with AllChrom plus™ software. A timeline program, which could change the detection gain during sample separation and detection, was used to make it possible to get low DA and high metabolites concentration data in dialysate through one injection.

Real-time Neurotransmitter Level Measurements

Real-time neurotransmitter levels were assayed by measuring the faradaic current at the respective oxidation potentials with a carbon fiber electrode inserted through the cannula.

RESULTS

In order to determine whether dopamine release is affected by uridine administration, animals provided UMP in their diets were assessed for dopamine production, both during and following neuron depolarization. FIGS. 1A-E depict the release profiles of a single uridine-fed rat and a single control rat over repeated stimulations. UMP administration enhanced release of DA (B) and 5-HT (E) both during and after depolarization. DOPAC (A), 5-HIAA (C), and HVA (D) exhibited lower basal levels in the UMP-fed animals, and release was increased, although by a smaller margin than DA and 5-HT, after but not during stimulation. UMP did not affect the total levels of DA and 5-HT in the striatum, while total striatal levels of DOPAC, 5-HIAA, and HVA in the striatum and striatal extracellular fluid (ECF) were slightly reduced.

Figure 2:
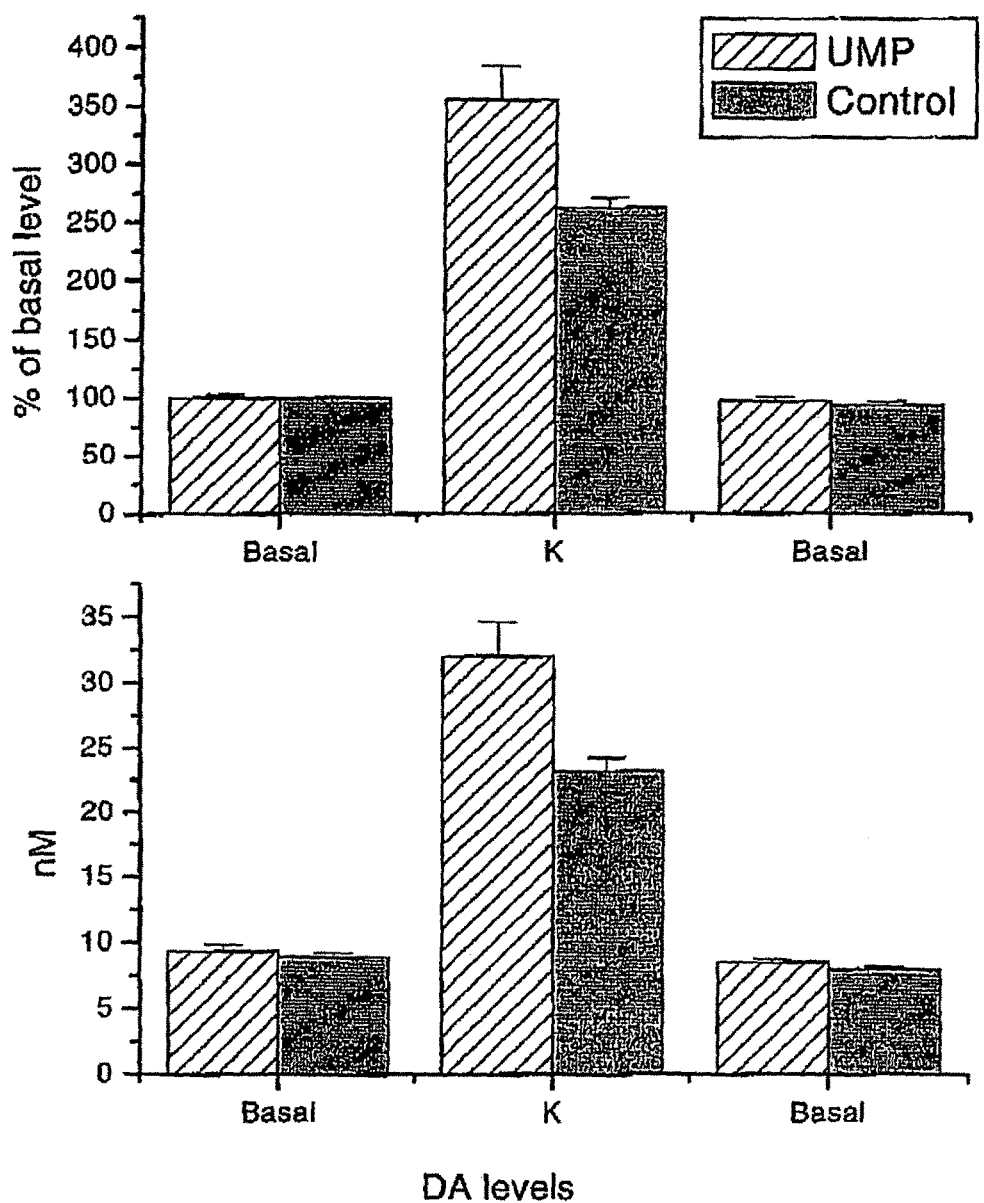
FIG. 2 depicts average dopamine release levels between uridine-fed rats and control rats (n=6 for each group) as a fold increase of basal level release (A) or total dopamine concentration (B). Dopamine release was measured release before, during (k) and after local depolarization with potassium.

FIG. 2 depicts the average values for DA release from 6 uridine-fed rats and a 6 control rats, expressed both as total amount of DA (bottom panel) and as a percentage of basal level (top panel).

In conclusion, UMP administration enhanced the amount of DA and 5-HT released from the striatum upon depolarization, and decreased total striatal levels of DA metabolites. Thus, administration of uridine and its metabolites or derivatives is an effective strategy for treating diseases characterized by decreased DA release, such as Parkinson's disease.

What is claimed is:

1. A method of treating Parkinson's disease in a subject having Parkinson's disease comprising orally administering to the subject in need of such treatment a composition having uridine or a uridine monophosphate, and a choline source, wherein the uridine or uridine monophosphate is administered at a dose of about 200 to 800 mg per day and administration of the composition stimulates or enhances neuron dopamine levels in the brain of the subject.

2. The method of claim 1, wherein said uridine or uridine monophosphate stimulates or enhances neuron release of a 5-hydroxytryptamine, acetyl choline, GABA, glutamate, adenosine, or a combination thereof from said neuron.

3. The method of claim 1, wherein said choline source is a choline, a lecithin, a phosphatidylcholine, a acetylcholine, a citicoline or an alpha-glycerophosphorylcholine.

4. The method of claim 1, wherein the composition further comprises a vitamin.

5. The method according to claim 3, wherein the citicoline is a cytidine 5'-diphosphocholine.

6. The method according to claim 4, wherein the vitamin is thiamin, riboflavin, niacin, pantothenic acid, pyridoxine, cobalamine, folic acid, retinol, tocopherol, ascorbic acid, calciferol, or phylloquinone.

7. The method according to claim 1, wherein the composition further comprises zinc, iron, copper, manganese, calcium, cobalt, phosphorous, iodine, magnesium, selenium, chromium, molybdenum, boron, nickel, or vanadium.

8. A nutritional supplement for orally treating or reducing the incidence of Parkinson's disease comprising between about 200 and 800 mg per day of a uridine or a uridine monophosphate, and a choline source, at a dose sufficient to stimulate or enhance dopamine release from a neuron of a subject.

9. The composition of claim 8, wherein said composition is formulated for controlled or sustained release.

10. The composition of claim 8, wherein said choline source is a choline, a lecithin, a phosphatidylcholine, a acetylcholine, a citicoline or an alpha-glycerophosphorylcholine.

11. The composition of claim 10, wherein said citicoline is a cytidine 5'-diphosphocholine.

12. The composition of claim 8, wherein said nutritional supplement further comprises a vitamin.

* * * * *